Figure 3:
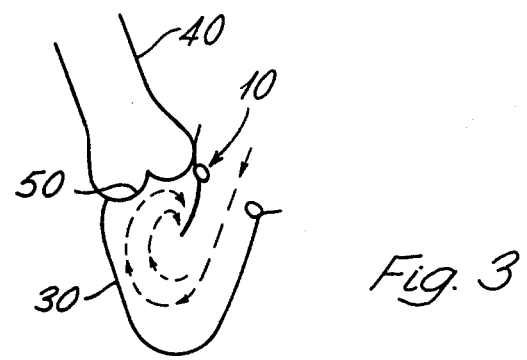

United States Patent [19]

Bellhouse et al.

[11] 4,204,283

[45] May 27, 1980

[54] PROSTHETIC VALVE

[75] Inventors: Brian J. Bellhouse, Islip, England; William G. Williams, Islington, Canada

[73] Assignee: National Research Development Corporation, London, England

[21] Appl. No.: 902,746

[22] Filed: May 3, 1978

[30] Foreign Application Priority Data

May 5, 1977 [GB] United Kingdom ............... 18895/77

[51] Int. Cl.$^2$ .............................................. A61F 1/22
[52] U.S. Cl. .......................................... 3/1.5; 137/527; 137/527.8
[58] Field of Search ............... 3/1.5, 1; 137/527, 527.8

[56] References Cited

U.S. PATENT DOCUMENTS

| | | | |
|---|---|---|---|
| 3,370,305 | 2/1968 | Goott et al. | 3/1.5 |
| 3,579,642 | 5/1971 | Heffernan et al. | 3/1.5 |
| 3,656,185 | 4/1972 | Carpentier | 3/1.5 |
| 3,812,542 | 5/1974 | Shiley | 3/1.5 |

OTHER PUBLICATIONS

"Evaluation of Two Prostheses for Total Replacement of the Mitral Valve" by F. S. Cross et al., The Journal of Thoracic & Cardiovascular Surgery, vol. 46, No. 6, Dec. 1963, pp. 719-725.

"Comparative Testing of Artificial Heart Valves in a Mock Circulation" by M. Klain et al., Prosthetic Heart Valves (Book) by Lyman A. Brewer III, Charles C. Thomas, Publisher, Springfield, Illinois, 1969, pp. 114-135, Liotta valve on page 123 relied upon.

Mitral Valve Prosthesis on page 16, The Bulletin of the Dow Corning Center For Aid To Medical Research, vol. 5, No. 4, 10/63, Midland, Mich.

*Primary Examiner*—Ronald L. Frinks
*Attorney, Agent, or Firm*—Cushman, Darby & Cushman

[57] ABSTRACT

A prosthetic valve, suitable for use as a mitral valve replacement, has a D-shaped annular seat-forming member and obturating flap, the flap having a major area formed by a rigid sheet of similar D-shape and extent for direct support on the seat when the valve is closed, and a flexible sheet hinge connecting the flap and annular member as a hinge along their straight edge portions. The rigid sheet is preferably scalloped around its free edge, with a flexible skirt being located across the incursions of this shaping, and is also preferably dished inwardly towards the valve.

11 Claims, 5 Drawing Figures

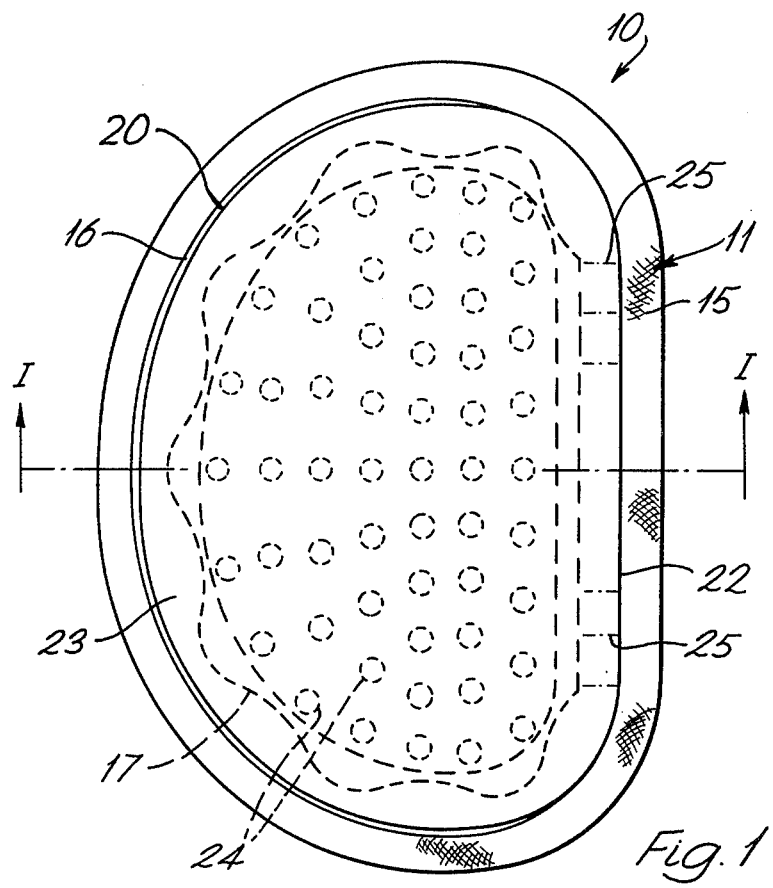
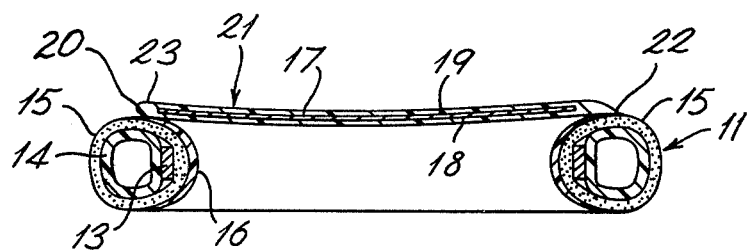

PROSTHETIC VALVE

This invention concerns prosthetic valves and it has been developed initially for use as a prosthetic mitral valve. However, while it is appropriate to describe the invention with reference to such use, it is to be understood that application may be made to other situations involving the handling of blood, such as oxygenators and dialysers.

While a considerable variety of proposals have been made in the past for prosthetic heart valves, those of such valves as are presently employed in clinical practice bear little resemblance to natural heart valve mechanisms. There is commonly a ball or disc element which is freely movable between an annular seat and members projecting therefrom to define a cage around the element. These cage members have proved to be a major thombogenic complication.

In contrast, the present invention more closely simulates the natural mitral valve and is based on a study of the latter valve as described in a paper entitled "Fluid Mechanics of a Model Mitral Valve and Left Ventricle" by B. J. Bellhouse in Cardiovascular Research, Vol. VI, No. 2, pages 199–210, March 1972, with a view to avoiding thrombogenic complications.

According to the present invention there is provided a prosthetic valve comprising: an annular member defining a valve seat around an aperture; and an obturating flap having a major area thereof in the form of a rigid sheet with a substantially straight edge portion, and having a minor area thereof in the form of a flexible sheet extending from said edge portion and connecting the same to said member to serve as a hinge; said flap being movable about said hinge between positions in which the flap is respectively engaged and disengaged with said seat to close and open said aperture, and said major area being of similar shape and extent to said seat so that the forces acting on said flap, when closed, are transmitted to said annular member predominantly through said stiff sheet.

An advantage of this form of valve is that the load on the flap, due to differential fluid pressure acting across it when closed, is not applied to the hinge.

In application as a prosthetic mitral valve, the annular member, flap and rigid sheet are each of general D-shape. The natural mitral annulus is of a similar shape and this form of valve conforms with the anatomy of the left ventricle. In addition the straight edge portion of a D-shape allows the provision of a sufficiently long hinge to reliably locate the flap in closing notwithstanding the flexible form of the hinge.

In a preferred form of the invention the free edge portion of the rigid sheet is scalloped, with flexible sheet material extending across the incursions of such shaping. This arrangement provides a flexible skirt which is located by the rigid sheet to ensure competence of the valve more reliably than may otherwise be the case with a purely rigid free edge portion. It is, in any case, preferred that the flap member be wholly covered with a layer of flexible blood-compatible material to define the skirt and hinge.

It is also preferred, for application as a mitral valve, that the rigid sheet is dished to provide opposed faces of convex and concave form which respectively face towards and away from the annular member. If the valve is located with the flap corresponding to the large anterior cusp of the natural mitral valve, the proposed dishing gives rise to blood flow patterns which correspond to those of the natural valve as described in the above-mentioned paper.

Also it is preferred that the annular member be of multiple component construction comprising an inner flexible tubular member held in the desired annular shape by a thinner stiffer member, such as a wire, with an overall outer covering of fabric. The tube and fabric provide a sewing ring which is readily penetrated for the purposes of suturing.

Figure 4:
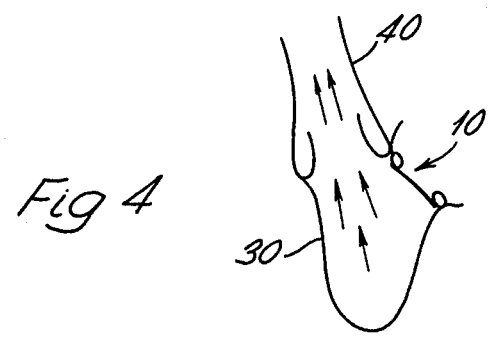
Figure 5:
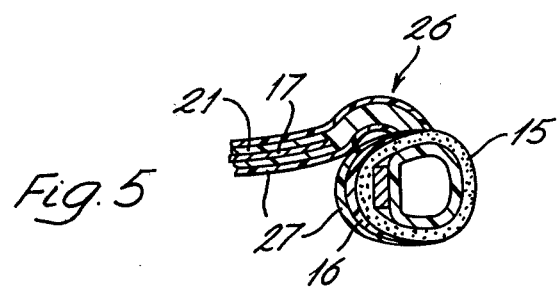

In order that the invention may be more clearly understood, the same will now be further described by way of example with reference to the accompanying drawings, in which:

FIGS. 1 and 2 diagrammatically illustrate a prosthetic mitral valve respectively in a plan view and cross-sectional view taken at I—I, FIGS. 3 and 4 schematically illustrate this valve when located in the heart, and respectively in open and closed conditions, and FIG. 5 diagrammatically illustrates a modified form of this valve in a cross-sectional view similar to that of FIG. 2.

The illustrated valve is denoted generally at 10 and comprises an annular member 11 and a flap 12.

The annular member 11 comprises a generally D-shaped metal wire 13 against which a tube 14 of flexible plastics material is held by enclosure of the wire and tube within an outer tubular sleeve 15 of fabric. The wire 13 is located radially innermost relative to the tube 14 and the D-shape, and the corresponding portion of the sleeve 15 is provided with an impermeable coating 16.

An initially preferred embodiment of this valve employs a wire of stainless steel, a tube of silicone rubber, a sleeve of knitted polyester fabric having its ends stitched together, and a coating of polyurethane.

The flap comprises a rigid sheet 17 of corresponding shape to the annular member 11, but slightly smaller in lateral dimensions to seat the free edge of the flap only on the member when located on the latter from one side thereof. The sheet 17 is dished to provide opposed convex and concave faces 18 and 19, and its curved free end portion 20 is scalloped. The sheet 17 is wholly coated with a flexible impermeable material 21 which extends beyond the free edge of the sheet to form a flexible sheet hinge 22 along the straight edge portion and a flexible skirt 23 along the scalloped edge portion 20. The hinge 22 is bonded to the straight portion of the annular member 11 to seat on the latter as described above, with the convex face 18 engaged on the member 11.

The above-described embodiment employs a rigid sheet of stainless steel and a coating of polyurethane, the sheet being formed with perforations 24 to key the coating.

The valve is shown in its intended location in FIGS. 3 and 4 with the flap assuming the position of the large anterior cusp of the natural mitral valve, and with the concave face facing into the left ventricle 30. The geometry of the flap and its location are then such that the valve opens wide early in diastole and is positioned at an angle approaching 90° by the formation of a vortex formed behind the flap during ventricular filling. This vortex formation is enhanced by the dished form of the flap. The flap is then moved towards closure by the combined effects of the vortex and the pressure gradient due to the decelerating flow through the valve. The valve is almost closed before the onset of ventricular systole, which ejects blood through the aorta 40 by way of the aortic valve 50, and so back flow through the prosthetic valve is negligible.

This action is consistent with that of the natural mitral valve as described in the above-mentioned paper.

The illustrated form of annular member is advantageous in affording easier penetration of its radially outer portions as a sewing ring for purposes of sututing. Also, the exposed fabric sleeve will allow tissue in-growth, while the impermeable coating will maintain the seat free of tissue.

While the invention has been described so far with more particular reference to a specific application and an initially preferred embodiment, this is not intended to be limiting. It has already been indicated in the introduction that the invention is capable of different applications, and the form of the embodiment is equally capable of variation. Indeed, modifications of the valve are being evaluated in further development of the invention.

One facet of such modifications involves what can be regarded as the provision of a perivalvular leak to inhibit thrombus formation and excessive tissue overgrowth in the region between the hinge and the annular member. One modification for this purpose can involve the provision of a plurality of transverse slits, as denoted in dotted line form at 25 in FIG. 1. However, this may be regarded as undesirable by virtue of the incompetence that is involved even though of low level. Another modification for this purpose involves preforming the hinge 22 at least over its end regions, and/or the skirt 23 adjacent to the ends of the hinge, to a curved shape extending away from the annular member 11 when unstressed. These preformed shapes will be such that, during closure, the remainder of the flap will seat first and the relevant shapes thereafter as the closure force increases with the onset of ventricular systole, with this last phase of closure giving rise to tunnelled configurations through which blood passes in the manner of jets to scour the hinge and regions and adjacent seat. Preforming of this kind is shown at 26 in FIG. 5 and is conveniently in the form of a single curved shape extending wholly along the hinge.

Another facet of the further modifications is aimed at enhancing the blood compatability of the valve. Again several different modifications are contemplated. In one such modification the impermeable material of the coating 16 is itself coated with a porous material to encourage the growth of a thin tissue layer, and a similar material is used as an outermost covering over the flap. It has been established that pore size is an important factor in regulating tissue layer thickness, with a pore size of about 10 μm being appropriate for the present purpose. In a similar modification the valve surfaces are coated with hydrophilic materials, and in another such modification the surfaces are coated with hydrophobic material. These modifications are also represented in FIG. 5 where 27 denotes the additional coatings.

We claim:

1. A prosthetic valve comprising: an annular member defining a valve seat around an aperture; and an obturating flap having a major area thereof in the form of a rigid sheet with a substantially straight edge portion, and having a minor area thereof in the form of a flexible sheet extending from along the whole length of said edge portion and connecting the flap to said member to serve as a hinge; said flap being movable about said hinge between positions in which the flap is respectively engaged and disengaged with said seat to close and open said aperture, and said major area being of similar shape and extent to said seat so that the forces acting on said flap, when closed, are transmitted to said annular member predominantly through said rigid sheet.

2. A valve according to claim 1 wherein said annular member, flap, and rigid sheet are each of general D-shape with said hinge extending along the straight edge portion of such shapes.

3. A valve according to claim 1 wherein said rigid sheet is dished providing opposed faces of convex and concave form respectively facing towards and away from said annular member.

4. A valve according to claim 1 wherein said hinge is preformed at least in the hinge end regions to curve away from said annular member.

5. A valve according to claim 1 wherein said annular member is of multiple component construction including an inner flexible tubular member held in the desired annular shape by a relatively stiff member within an overall fabric covering for these last two members.

6. A prosthetic valve comprising: an annular member defining a valve seat around an aperture; and an obturating flap having a major area thereof in the form of a rigid sheet with a substantially straight edge portion and a scalloped remaining edge portion, a first minor area thereof in the form of a flexible sheet extending from along the whole length of said straight edge portion and connecting the flap to said annular member to serve as a hinge, and secondary minor areas of flexible sheet material extending across the incursions of said scalloped edge portion, said flap being movable about said hinge between positions in which the flap is respectively engaged and disengaged with said seat to close and open said aperture, and said major area being of similar overall shape and extent to said seat so that the forces acting on said flap, when closed, are transmitted to said annular member predominantly through said rigid sheet.

7. A valve according to claim 6 wherein said rigid sheet is wholly covered with a layer of impermeable material which extends therefrom to define said first and second minor areas.

8. A valve according to claim 7 wherein said rigid sheet is perforated.

9. A prosthetic valve comprising: an annular member defining a valve seat around an aperture; and an obturating flap having a major area thereof in the form of a rigid sheet with a substantially straight edge portion, and having a minor area thereof in the form of a flexible sheet extending from along the whole length of said edge portion and connecting the flap to said member to serve as a hinge, said hinge being formed with a plurality of transverse slits therethrough, said flap being movable about said hinge between positions in which the flap is respectively engaged and disengaged with said seat to close and open said aperture, and said major area being of similar shape and extent to said seat so that the forces acting on said flap, when closed, are transmitted to said annular member predominantly through said rigid sheet.

10. A prosthetic valve comprising: an annular member defining a valve seat around an aperture; an obturating flap having a major area thereof in the form of a dished rigid sheet with a straight edge portion and wholly coated with a flexible impermeable material; and a hinge defined by an extension of said sheet coat material from along the whole length of said straight edge portion connecting said flap to said member with said dished major area providing opposed faces of convex and concave form respectively facing towards and away from said annular member; said flap being movable about said hinge between positions in which the flap is respectively engaged and disengaged with said seat to close and open said aperture, and said major area being of similar shape and extent to said seat so that the forces acting on said flap, when closed, are transmitted to said annular member predominantly through said rigid sheet.

11. A valve according to claim 10 wherein said rigid sheet is metal and said flexible impermeable material is polyurethane.

* * * * *